US012734470B2

(12) United States Patent
Mak

(10) Patent No.: US 12,734,470 B2
(45) Date of Patent: Sep. 15, 2026

(54) PREPARATION METHOD OF BISMUTH ION FILTER MEMBRANE AND APPLICATION THEREOF

(71) Applicant: WORK TOGETHER MARKETING CONSULTANT LIMITED, Hong Kong (CN)

(72) Inventor: ChiKui Mak, Hong Kong (CN)

(73) Assignee: WORK TOGETHER MARKETING CONSULTANT LIMITED, Hong Kong (CN)

( * ) Notice: Subject to any disclaimer, the term of this patent is extended or adjusted under 35 U.S.C. 154(b) by 0 days.

(21) Appl. No.: 19/055,475

(22) Filed: Feb. 17, 2025

(65) Prior Publication Data

US 2025/0186920 A1 Jun. 12, 2025

Related U.S. Application Data

(63) Continuation of application No. PCT/CN2023/122776, filed on Sep. 28, 2023.

(51) Int. Cl.

| | |
|---|---|
| ***B01D 46/00*** | (2022.01) |
| ***A61L 9/16*** | (2006.01) |
| ***B01D 39/14*** | (2006.01) |
| ***B01D 46/54*** | (2006.01) |
| *A62B 23/02* | (2006.01) |

(52) U.S. Cl.

CPC ............ *B01D 46/0001* (2013.01); *A61L 9/16* (2013.01); *B01D 39/14* (2013.01); *B01D 46/0028* (2013.01); *B01D 46/543* (2013.01); *A61L 2209/131* (2013.01); *A61L 2209/14* (2013.01); *A62B 23/02* (2013.01); *B01D 2239/0442* (2013.01); *B01D 2239/0464* (2013.01); *B01D 2239/0618* (2013.01); *B01D 2239/10* (2013.01); *B01D 2279/65* (2013.01)

(58) Field of Classification Search

CPC .. B01D 46/0001; B01D 39/14; B01D 46/543; B01D 2239/0442; B01D 2239/0464; B01D 2239/0618; B01D 2279/65; A61L 9/16; A61L 2209/131; A61L 2209/14; A62B 23/02

See application file for complete search history.

(56) References Cited

FOREIGN PATENT DOCUMENTS

| | | |
|---|---|---|
| CN | 114855448 A | 8/2022 |
| CN | 115448299 A | 12/2022 |
| CN | 116059836 A | 5/2023 |

*Primary Examiner* — Robert S Walters, Jr.

(74) *Attorney, Agent, or Firm* — Hemisphere Law, PLLC

(57) ABSTRACT

A preparation method of a bismuth ion filter membrane includes: placing a filter membrane substrate into a cleaning machine, adding a non-ionic chelating agent solution and water, treating the filter membrane substrate for 1-2 hours, then dehydrating the filter membrane substrate to obtain a filter membrane substrate A; adding the filter membrane substrate A and a chelated bismuth ion solution to a reactor, followed by adding a chelating agent solution, and reacting to obtain a filter membrane substrate embedded with bismuth ions; and dehydrating and drying the filter membrane substrate embedded with the bismuth ions to obtain the filter membrane. Due to the bismuth ions, it can develop bactericidal effects within a distance of 1-3 feet and also enhance negative oxygen ions. Using the bismuth ions to make filter membranes and masks provides a cost-effective material, which is ten times cheaper than silver ions, making it economically advantageous.

19 Claims, No Drawings

PREPARATION METHOD OF BISMUTH ION FILTER MEMBRANE AND APPLICATION THEREOF

CROSS-REFERENCE TO RELATED APPLICATIONS

This application is a continuation of International Patent Application No. PCT/CN2023/122776, filed Sep. 28, 2023, which claims the priority of Chinese Patent Application No. 202210995325.2, filed Aug. 18, 2023, both of which are herein incorporated by reference in their entirety.

TECHNICAL FIELD

The disclosure relates to the field of filter membrane preparation technologies, and more particularly to a preparation method of a bismuth ion filter membrane and an application thereof.

BACKGROUND

In recent years, the epidemic situation has been quite severe, and various ion-based antimicrobial materials have been applied on masks and air filter membranes. In addition to the past application of silver ions on the masks and the air filter membranes, materials such as platinum and gold have also developed. Experience has shown that platinum ions have better and more stable antimicrobial properties than the silver ions, and they also generate more negative oxygen ions in the masks, which can be indicated to be more advantageous than the silver ions. Unfortunately, the cost of production is relatively high, with the material being ten times more expensive than silver, making it less cost-effective. Moreover, when using gold ions for manufacturing, the cost becomes even higher.

In terms of application, it is found that bismuth ions can enhance the effects of other metal ions, especially in terms of the coronavirus disease 2019 (COVID-19) in recent years, the application of antimicrobial and disinfectant materials. Bismuth plays a very important role, as it not only enhances the ion's ability to kill bacteria and viruses, but also reduces cost and improves efficiency, and is an additive effect. For example, it is well aware that the silver ions can sterilize and disinfect, but the cost is relatively high. The platinum ions are also more effective in sterilization, but the cost is higher than silver. When the cost-effectiveness is not as good, the bismuth ions are added, which greatly improves the ability of silver and platinum materials, thus reducing the cost of using precious metals. In experiments, a same level of antimicrobial ability can reduce the cost of the precious metals by 5 to 10 times. Moreover, the bismuth ions have a photocatalytic effect, which is an additional antimicrobial ability. Under photocatalysis, the bismuth can enhance its micro-ethylene methoxycarbonylation (EMC) reaction, and it can kill bacteria within a distance of 1 to 3 feet. This is a very good added value and improves the practicality of material functionality.

It is known that most effective positive and negative electrode air purifiers on the market can produce about 10,000 negative oxygen ions. These are generated by electric stimulation, which may produce excessive ozone and hydroxyl groups. Of course, the negative oxygen ions produced by typical air purifiers on the market range from 2,000 to 6,000. However, a bismuth ion filter membrane can produce over 3 million negative oxygen ions without a need for electrical stimulation, which is a very economical and environmentally friendly application material.

In the related art, a Chinese patent application CN116059836A discloses a preparation method and an application of a bismuth ion filter membrane, which only loads bismuth ions onto a filter membrane substrate. The binding force between the bismuth ions and the filter membrane substrate is not strong, which may cause the bismuth ions to fall off during subsequent water washing processes, thereby reducing the antibacterial performance of the bismuth ion filter membrane. Therefore, the disclosure introduces the bismuth ions into flake graphite through chemical reactions, and then introduces the flake graphite onto a filter membrane substrate to improve the bonding strength between the bismuth ions and the filter membrane substrate, thereby enhancing the washability of a bismuth ion filter membrane. A Chinese patent application CN114855448A discloses the preparation of a sol by mixing bismuth tungstate and chitosan-based organic agents. It combines metal ion technology, organic matter technology, and photocatalyst technology, and is supplemented with graphene and/or activated carbon for adsorption and dust prevention. While the air permeability is not affected, it endows masks with long-acting, anti-haze, anti-epidemic and anti-coronavirus performance, the masks have a catalytic degradation function on harmful gases such as formaldehyde and benzene in air. It combines silver ions, inorganic agents, and organic agents, and the nano bismuth tungstate in the inorganic agents acts as a photocatalyst, which is different from the effect of the bismuth ions in the disclosure. At the same time, it does not provide that adding flake graphite and chitosan can enhance the binding force between the bismuth ions and the filter membrane substrate. In the Chinese patent application CN114855448A, the bismuth tungstate is an inorganic agent, which is an insoluble inorganic particle and cannot be adsorbed by chitosan to form chelated bismuth ions in the disclosure. However, a bismuth ion solution used in the disclosure is a water-soluble solution containing the bismuth ions, which can be adsorbed by the flake graphite and chitosan to form the chelated bismuth ions. Therefore, although the substance added in the Chinese patent application CN114855448A is the same as that in the disclosure, its function is completely different. Furthermore, a Chinese patent application CN115448299A discloses a high-conductivity graphene film and a preparation method thereof, which uses flake graphite to react with sulfuric acid and hydrogen peroxide to form flaky graphite. However, the Chinese patent application CN115448299A explicitly states in its specification that ultrasonic dispersion is not used to prevent damage to a crystal structure of graphene oxide by ultrasonic waves, which would lead to a reduction in a flake diameter of the graphene oxide. However, flaky graphite prepared in the disclosure requires ultrasonic treatment for 8 to 12 hours (h). Therefore, although a method of preparing the flaky graphite disclosed in the Chinese patent application CN115448299A is similar to that in the disclosure, an actual preparation process is entirely different. The reason is that the Chinese patent application CN115448299A primarily aims to enhance the electrical conductivity of the prepared graphene membrane, whereas the disclosure focuses on improving the adsorption properties of the flake graphite. Therefore, in a case of completely different preparation methods, functions, and effects, the flaky graphite in the Chinese patent application CN115448299A is not the same as the flaky graphite in the disclosure.

SUMMARY

In view of the shortcomings of the related art, the disclosure provides a preparation method of a bismuth ion filter membrane and an application thereof.

In order to achieve the above objectives, the disclosure provides the following technical solutions.

A preparation method of a bismuth ion filter membrane includes the following steps:

step (1), pre-treatment of a filter membrane substrate: placing the filter membrane substrate into a cleaning machine, adding a non-ionic chelating agent solution and water to the cleaning machine, soaking and stirring the filter membrane substrate, and then performing dehydration on the filter membrane substrate to obtain a filter membrane substrate A;

step (2), embedding of bismuth ions: adding the filter membrane substrate A obtained in the step (1) and a chelated bismuth ion solution to a reactor, followed by adding a non-ionic chelating agent solution to the reactor to perform a reaction to thereby obtain a filter membrane substrate embedded with the bismuth ions; and step (3), post-treatment: dehydrating and drying the filter membrane substrate embedded with the bismuth ions obtained in the step (2) to obtain the bismuth ion filter membrane.

In an embodiment, in the step (1), the filter membrane substrate is non-woven fabric, the non-ionic chelating agent solution is ammonium ethylenediaminetetraacetic acid (ammonium EDTA), and a concentration of the non-ionic chelating agent solution is 1 mole per liter (mol/L).

In an embodiment, a time for the soaking and stirring in the step (1) is 1 hour (h) to 2 h.

In an embodiment, in the step (1), a mass ratio of the filter membrane substrate to the water is 4-8:50, and a mass ratio of the non-ionic chelating agent solution to the water is 1:100-1,000.

In an embodiment, a preparation method of the chelated bismuth ion solution in the step (2) includes the following steps:

S1, adding flake graphite to a hydrogen peroxide ($H_2O_2$)/sulfuric acid ($H_2SO_4$) solution to obtain a flake graphite mixed solution, stirring the flake graphite mixed solution at room temperature for 10 minutes (min), followed by filtering and washing the flake graphite to obtain washed flake graphite, and then calcining the washed flake graphite in a nitrogen atmosphere at 500° C. to 600° C. for 10 min to 20 min to obtain pre-treated flake graphite; and adding the pre-treated flake graphite to an ethanol aqueous solution with a volume ratio of 1:1, performing an ultrasonic treatment on the pr-treated flake graphite under a stirring condition for 8 h to 12 h, and performing vacuum drying on the pre-treated flake graphite after the ultrasonic treatment to obtain flaky graphite;

S2, adding the flaky graphite obtained in the step S1 to an ethanol aqueous solution, then adding γ-glycidoxypropyltrimethoxysilane to the flaky graphite with the ethanol aqueous solution to obtain a mixture, performing a stirring reaction on the mixture to react to obtain a reaction product, and then performing filtering, washing, and drying on the reaction product to obtain pre-treated flaky graphite; and adding the pre-treated flaky graphite to dimethyl sulfoxide, followed by adding 2-guanidinobenzimidazole to obtain a pre-treated flaky graphite mixed solution, adjusting a pH of the pre-treated flaky graphite mixed solution to 10-12, and performing a constant-temperature reaction in the nitrogen atmosphere to obtain modified flaky graphite; and S3, adding 50 parts by weight of the modified flaky graphite in the step S2 to 920 parts by weight of deionized water, then adding 10 parts by weight of chitosan to obtain a modified flaky graphite mixed solution, adjusting a pH of the modified flaky graphite mixed solution to 2-3 to thereby obtain an adjusted flaky graphite mixed solution, stirring and reacting the adjusted flaky graphite mixed solution at 40° C. to 50° C. for 4 h to 6 h, followed by adding 20 parts by weight of bismuth ion solution to obtain a bismuth ion mixed solution, and reacting the bismuth ion mixed solution at 60° C. to 70° C. for 3 h to 4 h to obtain the chelated bismuth ion solution.

In an embodiment, in the step S2, a volume ratio of ethanol to water in the ethanol aqueous solution is 7-8:2-3, a mass ratio of the flaky graphite to the γ-glycidoxypropyltrimethoxysilane is 50:5-8, a temperature of the stirring reaction is 60° C. to 70° C., and a time of the stirring reaction is 2 h to 4 h; a mass ratio of the pre-treated flaky graphite to the 2-guanidinobenzimidazole is 50:4-6, a temperature of the constant-temperature reaction is 80° C. to 90° C., and a time of the constant-temperature reaction is 3 h to 5 h.

In an embodiment, in the step (2), the non-ionic chelating agent solution is ammonium EDTA, and a concentration of the non-ionic chelating agent solution is 1 mol/L; and a mass ratio of the filter membrane substrate A to the chelated bismuth ion solution is 4-8:50, and a mass ratio of the non-ionic chelating agent solution to the chelated bismuth ion solution is 1:100-1,000.

In an embodiment, in the step (2), a temperature of the reaction is 30° C. to 40° C., a time of the reaction is 10 min to 30 min, an air pressure of the reaction is 0.1 megapascals (MPa) to 0.15 MPa, and a pH of the reaction is 6 to 7.

In an embodiment, in the step (3), a temperature of the drying is 60° C. to 90° C., and a time of the drying is 4 h to 8 h.

The disclosure also protects the bismuth ion filter membrane obtained by the preparation method of the bismuth ion filter membrane.

The disclosure even still protects an application of the bismuth ion filter membrane on masks and air filter membranes.

Compared to the related art, the disclosure has the following beneficial effects.

1. The disclosure provides for the first time to apply the bismuth ions to the masks and the air filter membranes. The masks and filter membranes made of the bismuth ions can generate over 3 million negative oxygen ion range effects in test results. A specific value depends on a concentration of the bismuth ions used in a production process.

2. The bismuth ion filter membrane is prepared by the disclosure. Through oxidation acidification and ultrasonic treatment of the flake graphite, graphite with a well-developed layered crystal structure is obtained and oxygen-containing functional groups on a surface of graphite are increased, which is beneficial for subsequent reactions. Subsequently, the flaky graphite is reacted with the γ-glycidoxypropyltrimethoxysilane. This can improve the dispersibility of the flaky graphite and introduce active epoxy groups on the flaky graphite, which is beneficial for subsequent reactions. Next, the flaky graphite containing epoxy groups is reacted with the 2-guanidinobenzimidazole, thus the 2-guanidinobenzimidazole is grafted onto the graphite.

The benzimidazole rings and guanidine groups in the 2-guanidine benzimidazole serve dual purposes. On one hand, the guanidine groups have good antibacterial properties, which can significantly improve the antibacterial properties of the graphite. On the other hand, heterocyclic benzimidazole groups have a chelating effect on the bismuth ions, which can load more bismuth ions on the graphite in subsequent reactions. The bismuth ions and the guanidine groups can synergistically improve the antibacterial and long-lasting antibacterial properties of graphite. Then, the flaky graphite is reacted with the chitosan to load the chitosan on the surface of the graphite. Due to the presence of a large number of active groups such as amino and carboxyl groups, the chitosan can react with oxidized graphite, improving the bonding strength between the chitosan and the graphite. At the same time, the chitosan has good adsorption properties, further increasing a loading of the bismuth ions and a content of the bismuth ions in the graphite. It can also improve the bonding force between the graphite and the filter membrane substrate, making graphite containing the bismuth ions less likely to fall off, and making the prepared filter membrane have long-lasting antibacterial properties.

3. The bismuth ion filter membrane prepared by the disclosure is obtained by introducing the bismuth ions onto the flake graphite through chemical reactions, and then introducing the flake graphite into the filter membrane substrate. Through the photocatalytic effect of the bismuth ions, it can exert a sterilization effect within a distance of 1-3 feet. At the same time, due to a structure of the bismuth ions, it can also enhance negative oxygen ions generated by air filtration. Using the bismuth ions to make the filter membranes and the masks yields the most cost-effective materials, which are ten times cheaper than silver ions and more economical.

DETAILED DESCRIPTION OF EMBODIMENTS

The following will provide a clear and complete description of the technical solution of the disclosure in combination with specific embodiments. Apparently, the described embodiments are only a part of the embodiments of the disclosure, and not all of them. Based on the embodiments of the disclosure, all other embodiments obtained by those skilled in the art without creative labor are within the scope of protection of the disclosure.

All raw materials used in the embodiments of the disclosure can be obtained commercially. Among them, a non-ionic chelating agent, such as ammonium ethylenediaminetetraacetic acid (ammonium EDTA), and a bismuth ion solution can be purchased from Yatian Group. A concentration of bismuth ions in the bismuth ion solution is 5%.

Embodiment 1

A preparation method of a bismuth ion filter membrane includes the following steps.

Step (1), pre-treatment of a filter membrane substrate: 4 kilograms (kg) of non-woven fabric is placed into a cleaning machine, 50 kg of water and 500 milliliters (mL) of ammonium EDTA with a concentration of 1 mol/L are added to the cleaning machine. and soaking and stirring is performed for 1 h. After the soaking and stirring is completed, dehydration is performed on the filter membrane substrate to obtain a filter membrane substrate A.

Step (2), embedding of bismuth ions: the filter membrane substrate A (4 kg) obtained in the step (1) and 50 kg of chelated bismuth ion solution are added to a reactor, and 500 grams (g) of ammonium EDTA with a concentration of 1 mol/L is added to the reactor. A pH is adjusted to 6, and a reaction is performed at an air pressure of 0.1 MPa and a temperature of 30° C. for 10 min. After the reaction is complete, a filter membrane substrate embedded with the bismuth ions is obtained.

Step (3), post-treatment: the filter membrane substrate embedded with the bismuth ions obtained in the step (2) is dehydrated and then dried at 70° C. for 6 h to obtain the bismuth ion filter membrane.

A preparation method of the chelated bismuth ion solution includes the following steps.

S1, flake graphite is added to a $H_2O_2/H_2SO_4$ solution (with a volume ratio of $H_2O_2$ to $H_2SO_4$ of 1:3, a mass concentration of $H_2O_2$ of 30%, and a concentration of $H_2SO_4$ of 98%) to obtain a flake graphite mixed solution. The flake graphite mixed solution is stirred at room temperature for 10 min, followed by filtering and washing to obtain washed flake graphite. Then pre-treated flake graphite is obtained by calcining the washed flake graphite in a nitrogen atmosphere at 500° C. for 20 min. Subsequently, the pre-treated flake graphite is added to an ethanol aqueous solution with a volume ratio of 1:1, and subjected to an ultrasonic treatment under a stirring condition for 10 h. After vacuum drying, flaky graphite is obtained.

S2, 50 g of the flaky graphite in the step S1 is added to 920 g of deionized water, followed by adding 10 g of chitosan to obtain a flaky graphite mixed solution. A pH of the flaky graphite mixed solution is adjusted to 2.5, and the flaky graphite mixed solution is stirred and reacted at 45° C. for 5 hours. Then 20 g of bismuth ion solution is added to obtain a bismuth ion mixed solution, and the bismuth ion mixed solution is reacted at 65° C. for 3.5 h to obtain chelated bismuth ion solution.

Embodiment 2

A preparation method of a bismuth ion filter membrane includes the following steps.

Step (1), pre-treatment of a filter membrane substrate: 5 kg of non-woven fabric is placed into a cleaning machine, 50 kg of water and 500 mL of ammonium EDTA with a concentration of 1 mol/L are added to the cleaning machine, and soaking and stirring is performed for 1.5 h. After the soaking and stirring is completed, dehydration is performed on the filter membrane substrate to obtain a filter membrane substrate A.

Step (2), embedding of bismuth ions: the filter membrane substrate A (5 kg) obtained in the step (1) and 50 kg of chelated bismuth ion solution are added to a reactor, and 500 g of ammonium EDTA with a concentration of 1 mol/L is added to the reactor. A pH is adjusted to 6.5, and a reaction is performed at an air pressure of 0.1 MPa and a temperature of 40° C. for 10 min. After the reaction is complete, a filter membrane substrate embedded with the bismuth ions is obtained.

Step (3), post-treatment: the filter membrane substrate embedded with the bismuth ions obtained in the step (2) is dehydrated and then dried at 80° C. for 6 h to obtain the bismuth ion filter membrane.

A preparation method of the chelated bismuth ion solution includes the following steps.

S1, flake graphite is added to a $H_2O_2/H_2SO_4$ solution (with a volume ratio of $H_2O_2$ to $H_2SO_4$ of 1:3, a mass concentration of $H_2O_2$ of 30%, and a concentration of $H_2SO_4$ of 98%) to obtain a flake graphite mixed solution. The flake graphite mixed solution is stirred at room temperature for 10 min, followed by filtering and washing to obtain washed flake graphite. Then pre-treated flake graphite is obtained by calcining the washed flake graphite in a nitrogen atmosphere at 550° C. for 15 min. Subsequently, the pre-treated flake graphite is added to an ethanol aqueous solution with a volume ratio of 1:1, and subjected to an ultrasonic treatment under a stirring condition for 10 h. After vacuum drying, flaky graphite is obtained.

S2, 50 g of the flaky graphite in the step S1 is added to 920 g of deionized water, followed by adding 10 g of chitosan to obtain a flaky graphite mixed solution. A pH of the flaky graphite mixed solution is adjusted to 2.5, and the flaky graphite mixed solution is stirred and reacted at 45° C. for 5 hours. Then 20 g of bismuth ion solution is added to obtain a bismuth ion mixed solution, and the bismuth ion mixed solution is reacted at 65° C. for 3.5 h to obtain chelated bismuth ion solution.

Embodiment 3

A preparation method of a bismuth ion filter membrane includes the following steps.

Step (1), pre-treatment of a filter membrane substrate: 6 kg of non-woven fabric is placed into a cleaning machine, 50 kg of water and 500 mL of ammonium EDTA with a concentration of 1 mol/L are added to the cleaning machine, and soaking and stirring is performed for 1 h. After the soaking and stirring is completed, dehydration is performed on the filter membrane substrate to obtain a filter membrane substrate A.

Step (2), embedding of bismuth ions: the filter membrane substrate A (6 kg) obtained in the step (1) and 50 kg of chelated bismuth ion solution are added to a reactor, and 500 g of ammonium EDTA with a concentration of 1 mol/L is added to the reactor. A pH is adjusted to 7, and a reaction is performed at an air pressure of 0.15 MPa and a temperature of 40° C. for 20 min. After the reaction is complete, a filter membrane substrate embedded with the bismuth ions is obtained.

Step (3), post-treatment: the filter membrane substrate embedded with the bismuth ions obtained in the step (2) is dehydrated and then dried at 60° C. for 7 h to obtain the bismuth ion filter membrane.

A preparation method of the chelated bismuth ion solution includes the following steps.

S1, flake graphite is added to a $H_2O_2/H_2SO_4$ solution (with a volume ratio of $H_2O_2$ to $H_2SO_4$ of 1:3, a mass concentration of $H_2O_2$ of 30%, and a concentration of $H_2SO_4$ of 98%) to obtain a flake graphite mixed solution. The flake graphite mixed solution is stirred at room temperature for 10 min, followed by filtering and washing to obtain washed flake graphite. Then pre-treated flake graphite is obtained by calcining the washed flake graphite in a nitrogen atmosphere at 550° C. for 20 min. Subsequently, the pre-treated flake graphite is added to an ethanol aqueous solution with a volume ratio of 1:1, and subjected to an ultrasonic treatment under a stirring condition for 8 h. After vacuum drying, flaky graphite is obtained.

S2, 50 g of the flaky graphite in the step S1 is added to 920 g of deionized water, followed by adding 10 g of chitosan to obtain a flaky graphite mixed solution. A pH of the flaky graphite mixed solution is adjusted to 2, and the flaky graphite mixed solution is stirred and reacted at 40° C. for 6 hours. Then 20 g of bismuth ion solution is added to obtain a bismuth ion mixed solution, and the bismuth ion mixed solution is reacted at 60° C. for 4 h to obtain chelated bismuth ion solution.

Embodiment 4

A preparation method of a bismuth ion filter membrane includes the following steps.

Step (1), pre-treatment of a filter membrane substrate: 8 kg of non-woven fabric is placed into a cleaning machine, 50 kg of water and 500 mL of ammonium EDTA with a concentration of 1 mol/L are added to the cleaning machine, and soaking and stirring is performed for 2 h. After the soaking and stirring is completed, dehydration is performed on the filter membrane substrate to obtain a filter membrane substrate A.

Step (2), embedding of bismuth ions: the filter membrane substrate A (8 kg) obtained in the step (1) and 50 kg of chelated bismuth ion solution are added to a reactor, and 500 g of ammonium EDTA with a concentration of 1 mol/L is added to the reactor. A pH is adjusted to 7, and a reaction is performed at an air pressure of 0.15 MPa and a temperature of 40° C. for 30 min. After the reaction is complete, a filter membrane substrate embedded with the bismuth ions is obtained.

Step (3), post-treatment: the filter membrane substrate embedded with the bismuth ions obtained in the step (2) is dehydrated and then dried at 90° C. for 6 h to obtain the bismuth ion filter membrane.

A preparation method of the chelated bismuth ion solution includes the following steps.

S1, flake graphite is added to a $H_2O_2/H_2SO_4$ solution (with a volume ratio of $H_2O_2$ to $H_2SO_4$ of 1:3, a mass concentration of $H_2O_2$ of 30%, and a concentration of $H_2SO_4$ of 98%) to obtain a flake graphite mixed solution. The flake graphite mixed solution is stirred at room temperature for 10 min, followed by filtering and washing to obtain washed flake graphite. Then pre-treated flake graphite is obtained by calcining the washed flake graphite in a nitrogen atmosphere at 600° C. for 10 min. Subsequently, the pre-treated flake graphite is added to an ethanol aqueous solution with a volume ratio of 1:1, and subjected to an ultrasonic treatment under a stirring condition for 12 h. After vacuum drying, flaky graphite is obtained.

S2, 50 g of the flaky graphite in the step S1 is added to 920 g of deionized water, followed by adding 10 g of chitosan to obtain a flaky graphite mixed solution. A pH of the flaky graphite mixed solution is adjusted to 3, and the flaky graphite mixed solution is stirred and reacted at 50° C. for 4 hours. Then 20 g of bismuth ion solution is added to obtain a bismuth ion mixed solution, and the bismuth ion mixed solution is reacted at 70° C. for 3 h to obtain chelated bismuth ion solution.

Embodiment 5

A preparation method of a bismuth ion filter membrane includes the following steps.

Step (1), pre-treatment of a filter membrane substrate: 4 kg of non-woven fabric is placed into a cleaning machine, 50 kg of water and 500 mL of ammonium EDTA with a concentration of 1 mol/L are added to the cleaning machine, and soaking and stirring is performed for 1 h. After the soaking and stirring is completed, dehydration is performed on the filter membrane substrate to obtain a filter membrane substrate A.

Step (2), embedding of bismuth ions: the filter membrane substrate A (4 kg) obtained in the step (1) and 50 kg of chelated bismuth ion solution are added to a reactor, and 500 g of ammonium EDTA with a concentration of 1 mol/L is added to the reactor. A pH is adjusted to 6, and a reaction is performed at an air pressure of 0.1 MPa and a temperature of 30° C. for 10 min. After the reaction is complete, a filter membrane substrate embedded with the bismuth ions is obtained.

Step (3), post-treatment: the filter membrane substrate embedded with the bismuth ions obtained in the step (2) is dehydrated and then dried at 70° C. for 6 h to obtain the bismuth ion filter membrane.

A preparation method of the chelated bismuth ion solution includes the following steps.

S1, flake graphite is added to a $H_2O_2/H_2SO_4$ solution (with a volume ratio of $H_2O_2$ to $H_2SO_4$ of 1:3, a mass concentration of $H_2O_2$ of 30%, and a concentration of $H_2SO_4$ of 98%) to obtain a flake graphite mixed solution. The flake graphite mixed solution is stirred at room temperature for 10 min, followed by filtering and washing to obtain washed flake graphite. Then pre-treated flake graphite is obtained by calcining the washed flake graphite in a nitrogen atmosphere at 500° C. for 20 min. Subsequently, the pre-treated flake graphite is added to an ethanol aqueous solution with a volume ratio of 1:1, and subjected to an ultrasonic treatment under a stirring condition for 10 h. After vacuum drying, flaky graphite is obtained.

S2, 50 g of the flake graphite obtained in the step S1 is added to 800 g of ethanol aqueous solution (with a volume ratio of ethanol to water of 7.5:2.5), followed by adding 7 g of γ-glycidoxypropyltrimethoxysilane to obtain a mixture. A stirring reaction is performed on the mixture at 65° C. for 3 h to react to obtain a reaction product. After the stirring reaction is complete, filtering, washing, and drying are performed on the reaction product to obtain pre-treated flake graphite. Then 50 g of the pre-treated flaky graphite is added to 800 g of dimethyl sulfoxide, followed by adding 5 g of 2-guanidinobenzimidazole to obtain a pre-treated flaky graphite mixed solution and a pH of the pre-treated flaky graphite mixed solution is adjusted to 11. A constant-temperature reaction under the nitrogen atmosphere is performed at t 85° C. for 4 h to obtain modified flaky graphite.

S3, 50 g of the modified flaky graphite in the step S2 is added to 920 g of deionized water, followed by adding 10 g of chitosan to obtain a modified flaky graphite mixed solution. A pH of the modified flaky graphite mixed solution is adjusted to 2.5, and the modified flaky graphite mixed solution is stirred and reacted at 45° C. for 5 hours. Then 20 g of bismuth ion solution is added to obtain a bismuth ion mixed solution, and the bismuth ion mixed solution is reacted at 65° C. for 3.5 h to obtain chelated bismuth ion solution.

Comparative Embodiment 1

A preparation method of a bismuth ion filter membrane includes the following steps.

Step (1), pre-treatment of a filter membrane substrate: 4 kg of non-woven fabric is placed into a cleaning machine, 50 kg of water and 500 mL of ammonium EDTA with a concentration of 1 mol/L are added to the cleaning machine, and soaking and stirring is performed for 1 h. After the soaking and stirring is completed, dehydration is performed on the filter membrane substrate to obtain a filter membrane substrate A.

Step (2), embedding of bismuth ions: the filter membrane substrate A (4 kg) obtained in the step (1) and 50 kg of chelated bismuth ion solution are added to a reactor, and 500 g of ammonium EDTA with a concentration of 1 mol/L is added to the reactor. A pH is adjusted to 6, and a reaction is performed at an air pressure of 0.1 MPa and a temperature of 30° C. for 10 min. After the reaction is complete, a filter membrane substrate embedded with the bismuth ions is obtained.

Step (3), post-treatment: the filter membrane substrate embedded with the bismuth ions obtained in the step (2) is dehydrated and then dried at 70° C. for 6 h to obtain the bismuth ion filter membrane.

A preparation method of the chelated bismuth ion solution includes the following steps.

50 g of flake graphite is added to 930 g of deionized water, followed by adding 10 g of chitosan to obtain a flake graphite mixed solution. The flake graphite mixed solution is reacted at 65° C. for 3.5 h to obtain chelated bismuth ion solution.

Bismuth ion filter membranes prepared in the embodiments 1-5 and the comparative embodiment 1 are subjected to antibacterial testing in accordance with a standard GB/T 23763-2009. A test result is shown in Table 1 below.

TABLE 1

| Embodiments | Antibacterial rate of *Escherichia coli* (%) | Antibacterial rate of *Staphylococcus aureus* (%) |
|---|---|---|
| Embodiment 1 | 99.91 | 99.84 |
| Embodiment 2 | 99.94 | 99.79 |
| Embodiment 3 | 99.87 | 99.88 |
| Embodiment 4 | 99.92 | 99.82 |
| Embodiment 5 | 99.99 | 99.94 |
| Comparative embodiment 1 | 99.42 | 99.33 |

The bismuth ion filter membranes prepared in the embodiments 1-5 and the comparative embodiment 1 are used to make masks, which are then tested for antibacterial performance according to GB/T 20944.3-2008 "Antibacterial Performance Test" and the antibacterial performance is tested after 50 standard washes. A test result is shown in Table 2 below.

TABLE 2

| | Antibacterial rate of *Escherichia coli* (%) | | Antibacterial rate of *Staphylococcus aureus* (%) | |
|---|---|---|---|---|
| | unwashed | 50 washes | unwashed | 50 washes |
| Embodiment 1 | 99.82 | 96.21 | 99.67 | 95.84 |
| Embodiment 2 | 99.75 | 96.03 | 99.53 | 95.52 |
| Embodiment 3 | 99.71 | 96.34 | 99.62 | 95.66 |
| Embodiment 4 | 99.79 | 96.15 | 99.64 | 95.71 |
| Embodiment 5 | 99.99 | 98.52 | 99.99 | 98.13 |
| Comparative embodiment 1 | 99.21 | 58.16 | 99.09 | 52.79 |

Although the embodiments of the disclosure have been shown and described, it will be understood by those skilled in the art that various changes, modifications, substitutions, and variations can be made to these embodiments without departing from the principles and spirit of the disclosure. The scope of the disclosure is limited by the appended claims and their equivalents.

What is claimed is:

1. A preparation method of a bismuth ion filter membrane, comprising the following steps:

step (1), pre-treatment of a filter membrane substrate: placing the filter membrane substrate into a cleaning machine, adding a non-ionic chelating agent solution and water to the cleaning machine, soaking and stirring the filter membrane substrate, and then performing dehydration on the filter membrane substrate to obtain a filter membrane substrate A;

step (2), embedding of bismuth ions: adding the filter membrane substrate A obtained in the step (1) and a chelated bismuth ion solution to a reactor, followed by adding a non-ionic chelating agent solution to the reactor to perform a reaction to thereby obtain a filter membrane substrate embedded with the bismuth ions; and step (3), post-treatment: dehydrating and drying the filter membrane substrate embedded with the bismuth ions obtained in the step (2) to obtain the bismuth ion filter membrane; and wherein a preparation method of the chelated bismuth ion solution in the step (2) comprises the following steps:

S1, adding flake graphite to a hydrogen peroxide ($H_2O_2$)/sulfuric acid ($H_2SO_4$) solution to obtain a flake graphite mixed solution, stirring the flake graphite mixed solution at room temperature for 10 minutes (min), followed by filtering and washing the flake graphite to obtain washed flake graphite, and then calcining the washed flake graphite in a nitrogen atmosphere at 500° C. to 600° C. for 10 min to 20 min to obtain pre-treated flake graphite; and adding the pre-treated flake graphite to an ethanol aqueous solution with a volume ratio of 1:1, performing an ultrasonic treatment on the pre-treated flake graphite under a stirring condition for 8 hours (h) to 12 h, and performing vacuum drying on the pre-treated flake graphite after the ultrasonic treatment to obtain flaky graphite;

S2, adding the flaky graphite obtained in the step S1 to an ethanol aqueous solution, then adding γ-glycidoxypropyltrimethoxysilane to the flaky graphite with the ethanol aqueous solution to obtain a mixture, performing a stirring reaction on the mixture to react to obtain a reaction product, and then performing filtering, washing, and drying on the reaction product to obtain pre-treated flaky graphite; and adding the pre-treated flaky graphite to dimethyl sulfoxide, followed by adding 2-guanidinobenzimidazole to obtain a pre-treated flaky graphite mixed solution, adjusting a pH of the pre-treated flaky graphite mixed solution to 10-12, and performing a constant-temperature reaction in a nitrogen atmosphere to obtain modified flaky graphite; and S3, adding 50 parts by weight of the modified flaky graphite in the step S2 to 920 parts by weight of deionized water, then adding 10 parts by weight of chitosan to obtain a modified flaky graphite mixed solution, adjusting a pH of the modified flaky graphite mixed solution to 2-3 to thereby obtain an adjusted flaky graphite mixed solution, stirring and reacting the adjusted flaky graphite mixed solution at 40° C. to 50° C. for 4 h to 6 h, followed by adding 20 parts by weight of bismuth ion solution to obtain a bismuth ion mixed solution, and reacting the bismuth ion mixed solution at 60° C. to 70° C. for 3 h to 4 h to obtain the chelated bismuth ion solution.

2. The preparation method of the bismuth ion filter membrane as claimed in claim 1, wherein in the step S2, a volume ratio of ethanol to water in the ethanol aqueous solution is 7-8:2-3, a mass ratio of the flaky graphite to the γ-glycidoxypropyltrimethoxysilane is 50:5-8, a temperature of the stirring reaction is 60° C. to 70° C., and a time of the stirring reaction is 2 h to 4 h; a mass ratio of the pre-treated flaky graphite to the 2-guanidinobenzimidazole is 50:4-6, a temperature of the constant-temperature reaction is 80° C. to 90° C., and a time of the constant-temperature reaction is 3 h to 5 h.

3. The preparation method of the bismuth ion filter membrane as claimed in claim 1, wherein in the step (1), the filter membrane substrate is non-woven fabric, the non-ionic chelating agent solution is ammonium ethylenediaminetetraacetic acid (ammonium EDTA), and a concentration of the non-ionic chelating agent solution is 1 mole per liter (mol/L).

4. The preparation method of the bismuth ion filter membrane as claimed in claim 1, wherein a time for the performing soaking and stirring in the step (1) is 1 h to 2 h.

5. The preparation method of the bismuth ion filter membrane as claimed in claim 1, wherein in the step (1), a mass ratio of the filter membrane substrate to the water is 4-8:50, and a mass ratio of the non-ionic chelating agent solution to the water is 1:100-1,000.

6. The preparation method of the bismuth ion filter membrane as claimed in claim 1, wherein in the step (2), the non-ionic chelating agent solution is ammonium EDTA, and a concentration of the non-ionic chelating agent solution is 1 mol/L.

7. The preparation method of the bismuth ion filter membrane as claimed in claim 1, wherein in the step (2), a mass ratio of the filter membrane substrate A to the chelated bismuth ion solution is 4-8:50, and a mass ratio of the non-ionic chelating agent solution to the chelated bismuth ion solution is 1:100-1,000.

8. The preparation method of the bismuth ion filter membrane as claimed in claim 1, wherein in the step (2), a temperature of the reaction is 30° C. to 40° C., a time of the reaction is 10 min to 30 min, an air pressure of the reaction is 0.1 megapascals (MPa) to 0.15 MPa, and a pH of the reaction is 6 to 7.

9. The preparation method of the bismuth ion filter membrane as claimed in claim 1, wherein in the step (3), a temperature of the drying is 60° C. to 90° C., and a time of the drying is 4 h to 8 h.

10. The bismuth ion filter membrane obtained by the preparation method of the bismuth ion filter membrane as claimed in claim 1.

11. A preparation method of a bismuth ion filter membrane, comprising the following steps:

step (1), pre-treatment of a filter membrane substrate: placing the filter membrane substrate into a cleaning machine, adding a non-ionic chelating agent solution and water to the cleaning machine, soaking and stirring the filter membrane substrate, and then performing dehydration on the filter membrane substrate to obtain a filter membrane substrate A;

step (2), embedding of bismuth ions: adding the filter membrane substrate A obtained in the step (1) and a chelated bismuth ion solution to a reactor, followed by adding a non-ionic chelating agent solution to the reactor to perform a reaction to thereby obtain a filter membrane substrate embedded with the bismuth ions; and step (3), post-treatment: dehydrating and drying the filter membrane substrate embedded with the bismuth ions obtained in the step (2) to obtain the bismuth ion filter membrane; and wherein a preparation method of the chelated bismuth ion solution in the step (2) comprises the following steps:

S1, adding flake graphite to a $H_2O_2/H_2SO_4$ solution to obtain a flake graphite mixed solution, stirring the flake graphite mixed solution at room temperature for 10 min, followed by filtering and washing the flake graphite to obtain washed flake graphite, and then calcining the washed flake graphite in a nitrogen atmosphere at 500° C. to 600° C. for 10 min to 20 min to obtain pre-treated flake graphite; and adding the pre-treated flake graphite to an ethanol aqueous solution with a volume ratio of 1:1, performing an ultrasonic treatment on the pre-treated flake graphite under a stirring condition for 8 h to 12 h, and performing vacuum drying on the pre-treated flake graphite after the ultrasonic treatment to obtain flaky graphite; and S2, adding 50 parts by weight of the flaky graphite in the step S1 to 920 parts by weight of deionized water, then adding 10 parts by weight of chitosan to obtain a flaky graphite mixed solution, adjusting a pH of the flaky graphite mixed solution to 2-3 to thereby obtain an adjusted flaky graphite mixed solution, stirring and reacting the adjusted flaky graphite mixed solution at 40° C. to 50° C. for 4 h to 6 h, followed by adding 20 parts by weight of bismuth ion solution to obtain a bismuth ion mixed solution, and reacting the bismuth ion mixed solution at 60° C. to 70° C. for 3 h to 4 h to obtain the chelated bismuth ion solution.

12. The preparation method of the bismuth ion filter membrane as claimed in claim 11, wherein in the step (1), the filter membrane substrate is non-woven fabric, the non-ionic chelating agent solution is ammonium EDTA, and a concentration of the non-ionic chelating agent solution is 1 mol/L.

13. The preparation method of the bismuth ion filter membrane as claimed in claim 11, wherein a time for the performing soaking and stirring in the step (1) is 1 h to 2 h.

14. The preparation method of the bismuth ion filter membrane as claimed in claim 11, wherein in the step (1), a mass ratio of the filter membrane substrate to the water is 4-8:50, and a mass ratio of the non-ionic chelating agent solution to the water is 1:100-1,000.

15. The preparation method of the bismuth ion filter membrane as claimed in claim 11, wherein in the step (2), the non-ionic chelating agent solution is ammonium EDTA, and a concentration of the non-ionic chelating agent solution is 1 mol/L.

16. The preparation method of the bismuth ion filter membrane as claimed in claim 11, wherein in the step (2), a mass ratio of the filter membrane substrate A to the chelated bismuth ion solution is 4-8:50, and a mass ratio of the non-ionic chelating agent solution to the chelated bismuth ion solution is 1:100-1,000.

17. The preparation method of the bismuth ion filter membrane as claimed in claim 11, wherein in the step (2), a temperature of the reaction is 30° C. to 40° C., a time of the reaction is 10 min to 30 min, an air pressure of the reaction is 0.1 MPa to 0.15 MPa, and a pH of the reaction is 6 to 7.

18. The preparation method of the bismuth ion filter membrane as claimed in claim 11, wherein in the step (3), a temperature of the drying is 60° C. to 90° C., and a time of the drying is 4 h to 8 h.

19. The preparation method of the bismuth ion filter membrane as claimed in claim 11, wherein in the step S1, a volume ratio of $H_2O_2$ to $H_2SO_4$ is 1:3, a concentration of $H_2O_2$ is 30%, and a mass concentration of $H_2SO_4$ is 98%.

* * * * *